(12) United States Patent
Schaller

(10) Patent No.: US 9,655,613 B2
(45) Date of Patent: May 23, 2017

(54) BELTLESS STAPLE CHAIN FOR CARTRIDGE AND CARTRIDGELESS SURGICAL STAPLERS

(71) Applicant: Cardica, Inc., Redwood City, CA (US)

(72) Inventor: David T. Schaller, Redwood City, CA (US)

(73) Assignee: Dextera Surgical Inc., Redwood City, CA (US)

(*) Notice: Subject to any disclaimer, the term of this patent is extended or adjusted under 35 U.S.C. 154(b) by 516 days.

(21) Appl. No.: 14/206,606

(22) Filed: Mar. 12, 2014

(65) Prior Publication Data

US 2014/0263557 A1    Sep. 18, 2014

Related U.S. Application Data

(60) Provisional application No. 61/781,196, filed on Mar. 14, 2013.

(51) Int. Cl.
*A61B 17/072* (2006.01)
*A61B 17/064* (2006.01)
*A61B 90/00* (2016.01)

(52) U.S. Cl.
CPC .... *A61B 17/0644* (2013.01); *A61B 17/07207* (2013.01); *A61B 2017/07271* (2013.01); *A61B 2017/07278* (2013.01); *A61B 2090/037* (2016.02)

(58) Field of Classification Search
CPC ....... A61B 17/068; A61B 17/10; A61B 17/06; A61B 17/04; A61B 17/0644; A61B 18/14
USPC ......... 227/176.1, 177.1, 178.1, 179.1, 180.1, 227/181.1, 182.1
See application file for complete search history.

(56) References Cited

U.S. PATENT DOCUMENTS

| 3,650,453 A * | 3/1972 | Smith, Jr. .......... A61B 17/0684 |
| | | 227/136 |
| 5,456,400 A * | 10/1995 | Shichman ............ A61B 17/064 |
| | | 227/176.1 |
| 6,391,038 B2 * | 5/2002 | Vargas ........................ 227/175.1 |

(Continued)

FOREIGN PATENT DOCUMENTS

WO    WO 2010054404    5/2010

OTHER PUBLICATIONS

Notification of Transmittal of the International Search Report and the Written Opinion of the International Searching Authority, PCT/US2014/028336, mailed Jul. 11, 2014.

*Primary Examiner* — Thanh Truong
*Assistant Examiner* — Dariush Seif
(74) *Attorney, Agent, or Firm* — Vista IP Law Group, LLP

(57) ABSTRACT

A surgical stapling device is configured for use in open and/or laparoscopic surgical procedures. The device includes a staple holder with a first support element and a second support element for supporting a beltless continuous staple chain. Each staple of the staple chain is configured to be frangibly separated from the staple chain to pierce and secure a target tissue when each staple is deployed. The device also includes a plurality of standoff members wherein each of the plurality of standoff members is configured to support one of each staple of the staple chain when the one of each staple is being deployed. The surgical stapling device may be a cartridge-based or a cartridge-less based staple device.

9 Claims, 19 Drawing Sheets

(56) References Cited

U.S. PATENT DOCUMENTS

| | | | | |
|---|---|---|---|---|
| 7,438,209 B1* | 10/2008 | Hess | A61B 17/0643 | 227/176.1 |
| 7,918,376 B1* | 4/2011 | Knodel | A61B 17/07207 | 227/175.1 |
| 7,934,630 B2* | 5/2011 | Shelton, IV | A61B 17/064 | 227/175.1 |
| 8,070,034 B1* | 12/2011 | Knodel | A61B 17/072 | 227/175.1 |
| 8,070,036 B1 | 12/2011 | Knodel | | |
| 8,096,457 B1* | 1/2012 | Manoux | A61B 17/07207 | 227/175.1 |
| 8,220,690 B2 | 7/2012 | Hess et al. | | |
| 8,225,980 B1* | 7/2012 | Rivera | A61B 17/07292 | 227/176.1 |
| 8,240,538 B1* | 8/2012 | Manoux | A61B 17/07207 | 227/178.1 |
| 8,261,958 B1* | 9/2012 | Knodel | A61B 17/064 | 227/176.1 |
| 8,317,072 B1* | 11/2012 | Knodel | A61B 17/07207 | 227/175.1 |
| 8,365,971 B1* | 2/2013 | Knodel | A61B 17/068 | 198/804 |
| 8,403,956 B1* | 3/2013 | Thompson | A61B 17/072 | 227/175.1 |
| 8,413,869 B2 | 4/2013 | Heinrich | | |
| 8,469,253 B1* | 6/2013 | Knodel | A61B 17/068 | 227/175.1 |
| 8,496,155 B2* | 7/2013 | Knodel | A61B 17/072 | 227/175.1 |
| 8,631,990 B1* | 1/2014 | Park | A61B 17/0644 | 227/175.2 |
| 8,631,992 B1* | 1/2014 | Hausen | A61B 17/0644 | 227/175.1 |
| 8,636,189 B1* | 1/2014 | Knodel | A61B 17/07207 | 227/175.1 |
| 8,662,369 B1* | 3/2014 | Manoux | A61B 17/068 | 227/175.1 |
| 8,985,427 B1* | 3/2015 | Manoux | A61B 17/068 | 227/175.1 |
| 8,998,951 B2* | 4/2015 | Knodel | B21G 7/02 | |
| 9,004,339 B1* | 4/2015 | Park | A61B 17/068 | 227/176.1 |
| 9,038,881 B1* | 5/2015 | Schaller | A61B 17/064 | 227/176.1 |
| 9,084,600 B1* | 7/2015 | Knodel | A61B 17/07207 | |
| 9,155,536 B1* | 10/2015 | Hausen | A61B 17/068 | |
| 9,168,039 B1* | 10/2015 | Knodel | A61B 17/07207 | |
| 9,192,377 B1* | 11/2015 | Schaller | A61B 17/0644 | |
| 9,386,986 B2* | 7/2016 | White | A61B 17/0644 | |
| 2009/0065552 A1* | 3/2009 | Knodel | A61B 17/072 | 227/180.1 |
| 2012/0080497 A1* | 4/2012 | White | A61B 17/0644 | 227/177.1 |
| 2016/0058445 A1* | 3/2016 | Morgan | A61B 17/0644 | 227/177.1 |

* cited by examiner

BELTLESS STAPLE CHAIN FOR CARTRIDGE AND CARTRIDGELESS SURGICAL STAPLERS

CROSS-REFERENCE TO RELATED APPLICATION(S)

This patent application claims priority to Provisional U.S. Patent Application Ser. No. 61/781,196, filed Mar. 14, 2013, which is herein incorporated by reference in its entirety.

FIELD OF THE INVENTION

The invention generally relates to surgical staplers and stapling devices.

BACKGROUND

An endocutter is a surgical tool that staples and cuts tissue to transect that tissue while leaving the cut ends hemostatic. An endocutter is small enough in diameter for use in minimally invasive surgery, where access to a surgical site is obtained through a trocar, port, or small incision in the body. A linear cutter is a larger version of an endocutter, and is used to transect portions of the gastrointestinal tract. A typical endocutter receives at its distal end a disposable single-use staple cartridge with several rows of staples, and includes an anvil to oppose and deform the deployed staples in the staple cartridge. The staples may be held in individual pockets, with staple drivers underneath each staple. As a wedge advances into the cartridge, that wedge sequentially pushes a number of staple drivers upward, and the staple drivers in turn both linearly push each corresponding staple upward out of its pocket, deforming it against an anvil.

During actuation of an endocutter, the cartridge fires all of the staples that it holds. In order to deploy more staples, the endocutter must be moved away from the surgical site and removed from the patient, after which the old cartridge is exchanged for a new cartridge. The endocutter is then reinserted into the patient.

SUMMARY OF THE INVENTION

A surgical stapling device is configured for use in open and/or laparoscopic surgical procedures. The device includes a staple holder with a first support element and a second support element for supporting a continuous staple chain. Each staple of the staple chain is configured to be frangibly separated from the staple chain to pierce and secure a target tissue when each staple is deployed. The device also includes a plurality of standoff members wherein each of the plurality of standoff members is configured to support one of each staple of the staple chain when the one of each staple is being deployed. The surgical stapling device may be a cartridge-based or a cartridge-less staple device.

As mentioned, a staple holder of the surgical stapling device may include a first support element and a second support element for supporting a continuous staple chain that is belt-less or without a feeder belt. The first support element may provide lateral support to the staple chain, while the second support element provides vertical support to the staple chain. In addition, each of the plurality of standoff members may be respectively coupled to the first support element along various locations or positions along a length or surface of the first support element. The arrangement is such that each staple of the staple chain is being held in place by a respective or corresponding standoff member while one of each staple of the staple chain is being deployed. The arrangement of the staple chain is that each staple of the staple chain is frangibly coupled to at least one other staple of the staple chain. The staple chain is comprised of an end portion of one of each staple of the staple chain being frangibly coupled to a head portion of another one of each staple of the staple chain. One of each staple of the staple chain is frangibly separated from another one of each staple of the staple chain at a frangibly connection region, location, or point when the one of each staple of the staple chain is being deployed. The frangibly connection region, location, or point is where an end portion of one of each staple of the staple chain meets, connects, couples, or joins to a head portion of another one of each staple of the staple chain. A wedge element, being deployed within the staple holder, configured to directly act on or push each staple of the staple chain to deploy each staple.

BRIEF DESCRIPTION OF THE DRAWINGS

The use of the same reference symbols in different figures indicates similar or identical items.

DETAILED DESCRIPTION

U.S. patent application Ser. No. 12/400,790, entitled "True Multi-Fire Surgical Stapler Configured to Fire Staples of Different Sizes", filed on Mar. 9, 2009 (the "Feeder Belt Document"), is hereby incorporated by reference herein in its entirety. The Feeder Belt Document describes exemplary feeder belts used in a surgical stapler, to which plurality of staples are frangibly connected. Because new staples are fed to an end effector of a surgical stapler by the feeder belts for sequential deployment, the surgical stapler of the Feeder Belt Document does not need or utilize plurality of single-use cartridges in order to deploy multiple sets of staples.

Figure 1:
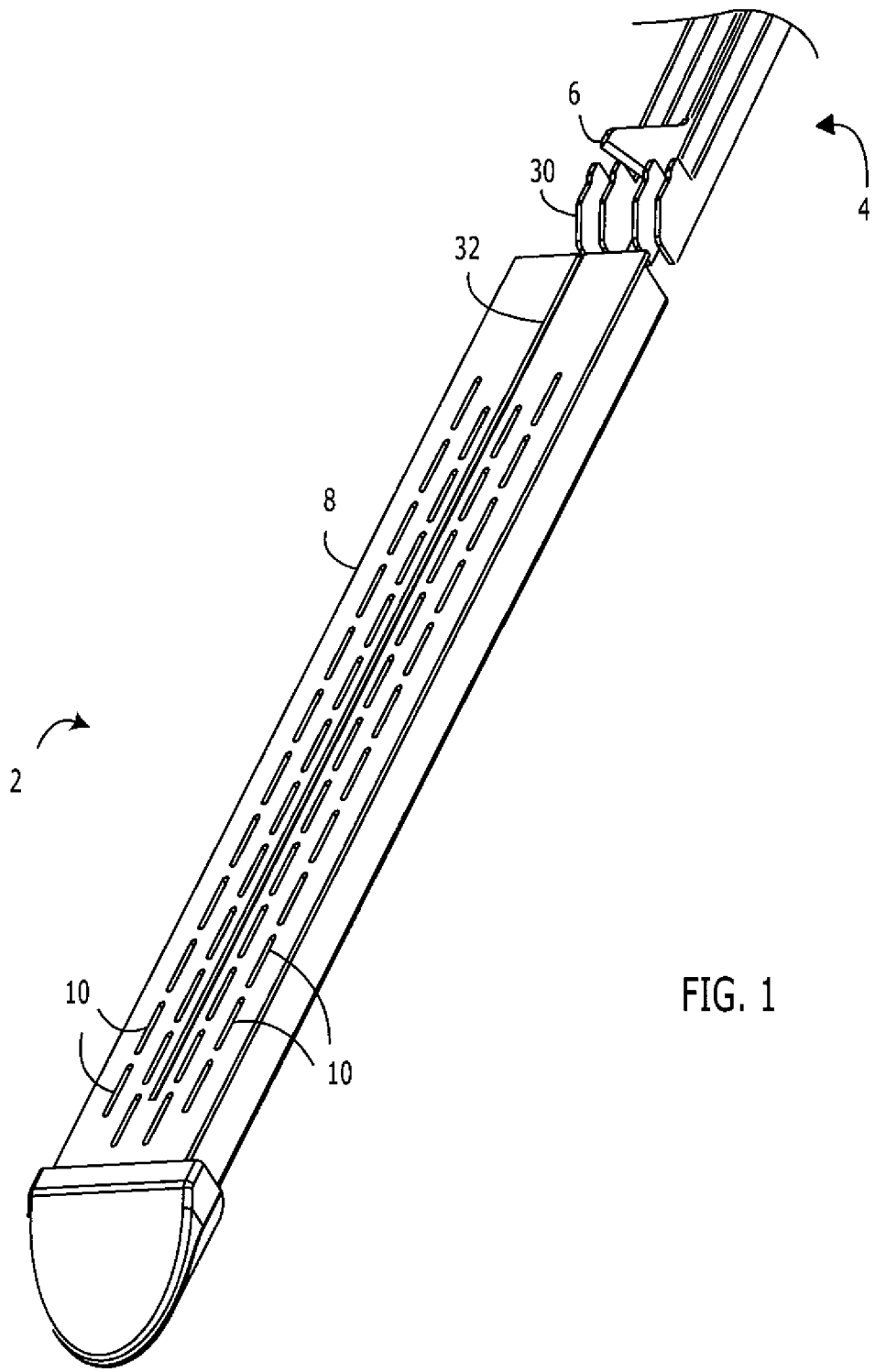
FIG. 1 illustrates a perspective view of an exemplary cartridge and exemplary wedge assembly.

As is commonly used in the medical device industry, particularly in the surgical stapler business, the term "cartridge" means, and is expressly defined in this document to mean, a portion of a surgical stapler that holds at least one staple, and that is insertable within and releasably connected to a remainder of the surgical stapler. Referring to FIG. 1, an exemplary cartridge 2 is shown, along with an exemplary wedge assembly 4 and knife 6. The cartridge 2 may be utilized in conjunction with any surgical stapler that is capable of receiving it, and that includes at least a wedge assembly 4 capable of moving into the cartridge 2 to deploy staples (as described in greater detail below) and then moving out of the cartridge 2 to allow the spent cartridge 2 to be removed from the surgical stapler. The cartridge 2 may be received in a remainder of a surgical stapler in any suitable manner, such as by a pressure fit or interference fit; passively or affirmatively; or in any other suitable manner. The cartridge 2 may be received at the distal end of a remainder of the surgical stapler, and/or along the side of a remainder of the surgical stapler. The cartridge 2 may be useful in conjunction with an articulated surgical stapler having an articulation proximal to the location at which the cartridge is attached to the stapler. Such an articulation may be, for example, as described in U.S. patent application Ser. No. 12/400,760, entitled "Articulated Surgical Instrument", filed on Mar. 9, 2009, or in U.S. patent application Ser. No. 12/612,614, entitled "Surgical Stapler with Variable Clamp Gap", filed on Nov. 4, 2009, both of which are hereby incorporated by reference in their entirety.

The cartridge 2 may be shaped in any suitable manner. As one example, the cartridge 2 may include an upper surface 8. The upper surface 8 may be generally flat, and generally rectangular. However, the upper surface 8 need not be generally flat along all or part of its area, and may be shaped in a manner other than rectangular. Further, the upper surface 8 need not be a discrete part of the cartridge 2, and instead simply may be a portion of a larger surface or area of the cartridge 2. The upper surface 8 of the cartridge 2 may include a plurality of openings 10 defined completely therethrough. As described in greater detail below, each opening 10 may be aligned with a corresponding staple, such that a staple may be deployed through each opening 10. Each opening 10 may be generally longitudinally-oriented, and generally rectangular in shape. Alternately, the orientation and/or shape of at least one opening 10 may be different from the other openings 10. The openings 10 may be organized into one or more generally-longitudinally-oriented rows, corresponding to the locations of staples in the cartridge 2. As another example, the openings 10 may be interconnected to form one or more larger openings, such that more than one staple may be deployed through a single opening 10. Alternately, the upper surface 8 may be omitted altogether, thereby rendering openings 10 superfluous.

Figure 2:
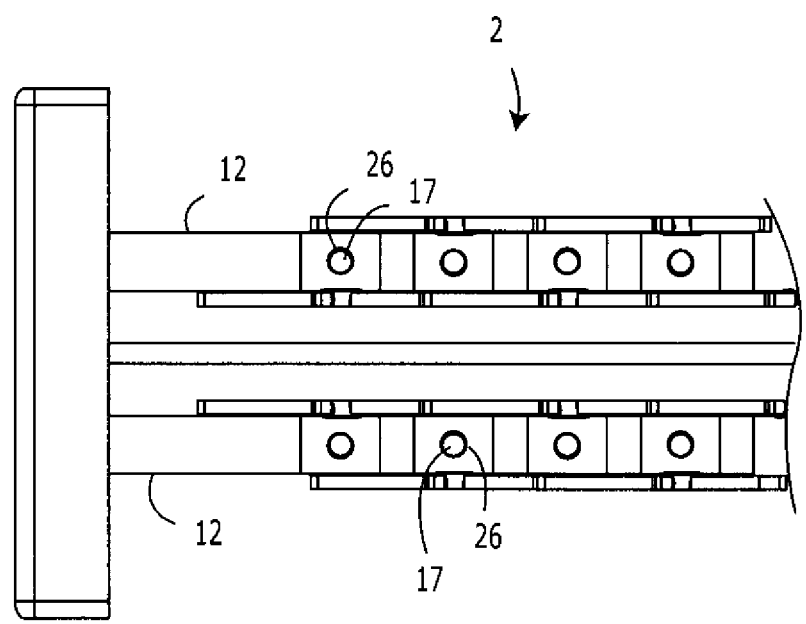
FIG. 2 illustrates a top cutaway view of the exemplary cartridge of FIG. 1.
Figure 3:
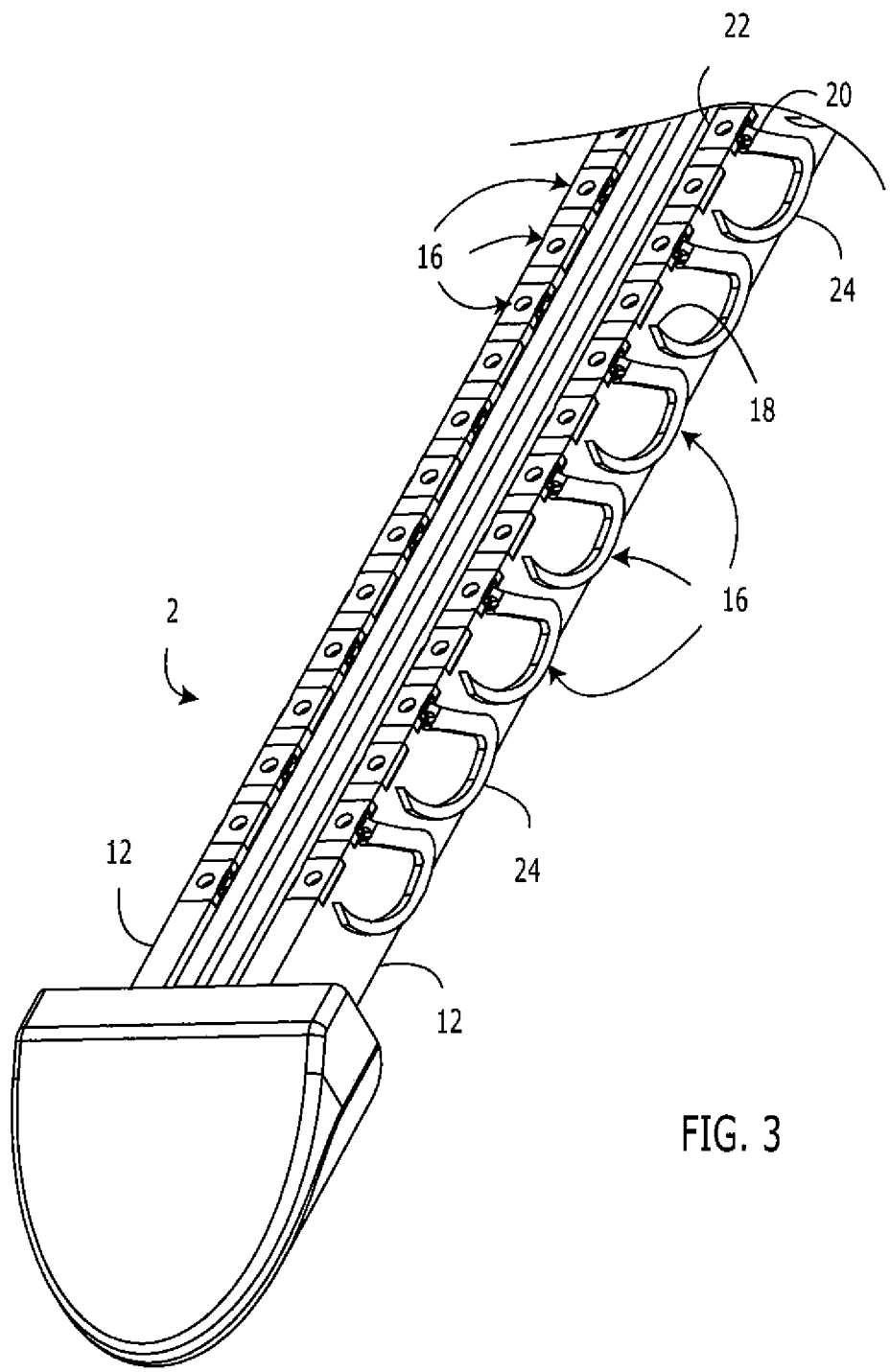
FIG. 3 illustrates a perspective cutaway view of the exemplary cartridge of FIG. 1.
Figure 4:
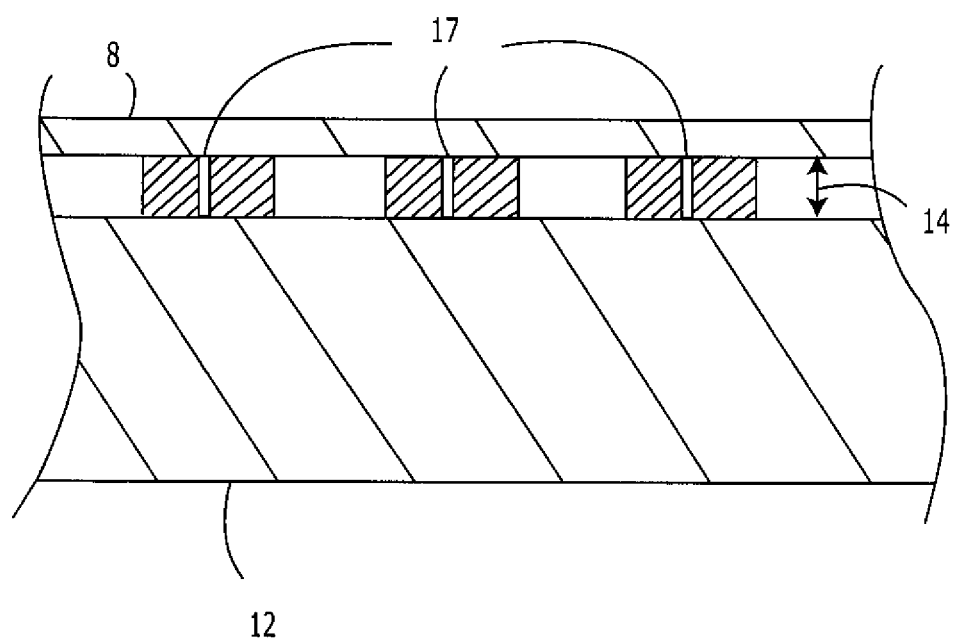
FIG. 4 illustrates a side cross-section view of the exemplary cartridge of FIG. 1, with staples omitted for clarity.

Referring also to FIGS. 2-4, the cartridge 2 also may include one or more rails 12. The rails 12 may be oriented generally longitudinally, and may be shaped generally as rectangular solids. At least one rail 12 may be dimensioned greater in lateral width than in vertical height, as seen most clearly in FIG. 3. As another example, at least one rail 12 may be oriented and/or shaped in any other suitable manner. The rails 12 may be spaced laterally apart from one another. The rails 12 may be fabricated from any suitable material, and in any suitable manner. At least one rail 12 may be vertically spaced apart from the upper surface 8 of the cartridge 2 by a gap 14. One or more pins 17 may extend from at least one rail 12 across the gap 14 to the upper surface 8. The pins 17 may be fabricated integrally with the corresponding rail 12 and/or upper surface 8, or may be fabricated separately and later connected thereto. At least one pin 17 may be generally cylindrical in shape. However, at least one pin 17 may be shaped differently. The pins 17 advantageously are shaped the same as one another, but at least one pin 17 may be shaped differently than at least one other pin 17.

A plurality of staples 16 may be affixed to and frangibly separable from the cartridge 2. The staples 16 may be shaped substantially in the same manner as the staples described in the Feeder Belt Document, or may be shaped in any other suitable manner. Each staple 16 may have a free end 18, and an opposite end 20 that is connected to a stem 22. The portion of the staple 16 between the free end 18 and the opposite end 20 may be referred to as the tine 24. The stem 22 of at least one staple 16 may be substantially perpendicular to the tine 24 of that staple 16. As another example, the stem 22 and tine 24 of a staple 16 may be oriented at a different angle to one another. The stem 22 may be substantially planar and rectangular, but may be shaped differently if desired. Each tine 24 may be fixed to the corresponding stem 22. Advantageously, the tine 24 and corresponding stem 22 are integral, and may be fabricated by stamping a piece of flat sheet metal, then bending the tine 24 and the stem 22 to the desired angle relative to one another. Advantageously, each staple 16 is positioned on a corresponding rail 12, such that the stem 22 is positioned on top of that rail 12. The thickness of the stem 22 may be substantially the same as the height of the gap 14 between each rail 12 and the upper surface 8. Alternately, the thickness of at least one stem 22 may be less than the height of the gap 14 between each rail 12 and the upper surface 8. Each staple 16 may be fixed to the upper surface 8 of the cartridge and/or to a rail 12, in any suitable manner. As one example, at least one stem 22 may include at least one aperture 26 defined therethrough. That aperture 26 may receive a corresponding pin 17 that extends from the upper surface 8 to a rail 12. As another example, at least one stem 22 may be welded to the top of a corresponding rail 12 and/or to the bottom of the upper surface 8. As another example, at least one stem may be affixed to the top of a corresponding rail 12 and/or to the bottom of the upper surface 8 by adhesive. As another example, at least one stem 22 may be pressure-fit between the upper surface 8 and the corresponding rail 12. As another example, at least one stem 22 may be fixed to a corresponding rail 12 and/or the upper surface 8 in two or more ways, such as, for example, by welding and by receiving a pin 17 through an aperture 26 in the stem 22. At least one staple 16 may be fabricated separately from a remainder of the cartridge 2, then affixed to the cartridge 2 as set forth above. Alternately, at least one staple 16 may be integral with a remainder of the cartridge 2.

The staples 16 may be arranged in the cartridge 2 in any suitable manner. As one example, one or more staples 16 may be arranged against a corresponding rail 12, with each stem 22 fixed to the corresponding rail 12. The staples 16 may be arranged relative to the rail 12 and to one another such that the tine 24 extending from a particular staple 16 is positioned on one lateral side of the rail 12, and the tine 24 extending from each longitudinally-adjacent staple 16 is positioned on the other lateral side of the rail 12. In this way, the tines 24 alternate sides relative to the rail 12 longitudinally along the rail 12, as seen most clearly in FIGS. 2-3. As another example, each staple 16 may include a single stem 22, with two tines 24 extending from it. Each tine 24 may extend from a lateral side opposed to the other. The stem 22 may be positioned on top of a rail 12, with each stem 22 fixed to the corresponding rail 12, and with each tine 24 positioned on a different lateral side of the corresponding rail 12. One tine 24 may be positioned longitudinally distal to the other tine 24 extending from the same stem 22. Such staples 16 may be arranged relative to the rail 12 such that the tines 24 alternate sides relative to the rail 12 longitudinally along the rail 12. As another example, at least one staple 16 is integral with the upper surface 8, and is affixed to a remainder of the upper surface 8 at the end 20 of the tine 24. In such a configuration, the staple 16 may be fabricated by punching, stamping, or otherwise dislodging it from the upper surface 8, such that the staple 16 extends from one end of a corresponding opening 10 in the upper surface 8, and the opening 10 results from the fabrication of the staple 16 associated with it. Further, in such a configuration, the stem 22 may be omitted from the staple 16. Regardless of the particular configuration of the staples 16, each tine 24 may be positioned adjacent to a corresponding opening 10 in the upper surface 8, and/or may be affixed to the upper surface 8 in proximity to the corresponding opening 10.

At least part of each staple 16 may be frangibly affixed to a remainder of the cartridge 2. "Frangibly affixed" is defined to mean that at least part of each staple 16 is fixed to a remainder of the cartridge 2 in such a manner that it must be sheared or otherwise broken off from a remainder of the cartridge 2 to be removed therefrom. As one example, at least one staple 16 may be frangible at the junction between the stem 22 and the tine 24. Such a junction may have a weakened area to facilitate frangibility. As another example, at least one staple 16 may remain intact during deployment, and the stem 22 of the staple 16 is frangible from the corresponding rail 12 and/or the upper surface 8. As another example, where the tine 24 is integral with the upper surface 8, the tine 24 may be frangible at the junction between the tine 24 and the upper surface 8.

The cartridge 2 may be actuated, and the staples 16 deployed, substantially as set forth in the Feeder Belt Document, with the following general differences. The wedge assembly 4 includes one or more wedges 30 configured generally as set forth in the Feeder Belt Document. Initially, the wedge or wedges 30 may be positioned proximal to the cartridge 2. In this way, the wedge or wedges 30 do not interfere with the insertion of the cartridge 2 into a remainder of the surgical stapler. The cartridge 2 may be inserted into the stapler, or may already be present in the stapler, prior to actuation of the stapler. The wedge assembly 4 is moved distally, advantageously by sliding. As the wedge assembly 4 moves distally, it slides the wedge or wedges 30 distally as well. Advantageously, one wedge 30 slides along a corresponding row of staples 16 to sequentially deform staples 16 outward through the corresponding openings 10 in the upper surface 8, and then break staples 16 from the cartridge 2. Such deformation and later breakage of the staple may be as set forth generally in the Feeder Belt Document. As one example, the stem 22 of one or more staples 16 is held substantially in place by its affixation to a corresponding rail 12 and/or to the upper surface 8, as set forth above. As a wedge 30 slides distally relative to the staple 16, the wedge 30 first engages the tine 24 of that staple 16, causing the tine 24 to move upward and to rotate about the junction between the tine 24 and the stem 22. Rotation of the tine 24 upward causes the tine 24 to move up through a corresponding opening 10 in the upper surface 8, through tissue, and then move into contact with an anvil (not shown), such as set forth in the Feeder Belt Document. Contact between the tine 24 and the anvil deforms the tine 24 to its closed configuration. As the wedge 30 continues to move distally relative to the staple 16, both the wedge 30 and the tine 24 may be shaped such that the wedge 30 may continue to contact and exert force on the tine 24 after the tine 24 has been deformed. This force increases until the tine 24 is broken, sheared or otherwise separated from the stem 22. As another example, this force increases until the stem 22 is broken, sheared or otherwise separated from a remainder of the cartridge 2, such as from a corresponding rail 12 and/or the upper surface 8 of the cartridge 2. The wedge 30 thereby may sequentially separate the frangible staples 16 from a remainder of the cartridge 2.

A knife 6 also may be connected to the wedge assembly 4, and may slide upward through the corresponding knife slot 32 in the upper surface 8 as the wedge assembly 4 moves distally through the cartridge 2. The knife 6 may be actuated, and may cut tissue, substantially as set forth in the Feeder Belt Document. Optionally, the knife 6 may be omitted from the wedge assembly 4, if desired. The knife 6 may be configured to move into the cartridge 2, then move upward through and out of the knife slot 32, then slide along the knife slot 32, then move downward through the knife slot 32. In this way, the knife 6 may be held in a position in which it does not extend through the knife slot 32 both before and after it has cut tissue, in order to enhance safety for the user and the patient.

After the wedge assembly 4 has been actuated to deploy one or more of the staples 16, the cartridge 2 is spent. The wedge assembly 4 then may be retracted proximally through and then out of the proximal end of the cartridge 2. The spent cartridge 2 then may be removed from a remainder of the surgical stapler. If desired, a new cartridge 2 may then be inserted into the surgical stapler in place of the previous, spent cartridge 2. The new cartridge 2 may be actuated substantially as described above.

In addition, Cardica, Inc. of Redwood City, Calif. has developed a true multi-fire endocutter that is capable of firing multiple times without the need to utilize single-use-cartridges. That is, the true multi-fire endocutter is a cartridge-less device capable of firing multiple sets of staples without the need of reloading a new cartridge of staples for repeated firing. An example of such an endocutter is described in U.S. patent application Ser. No. 12/263,171, entitled "Multiple-Use Surgical Stapler", filed on Oct. 31, 2008 (the "Endocutter Application"), which is hereby incorporated by reference in its entirety.

Figure 5:
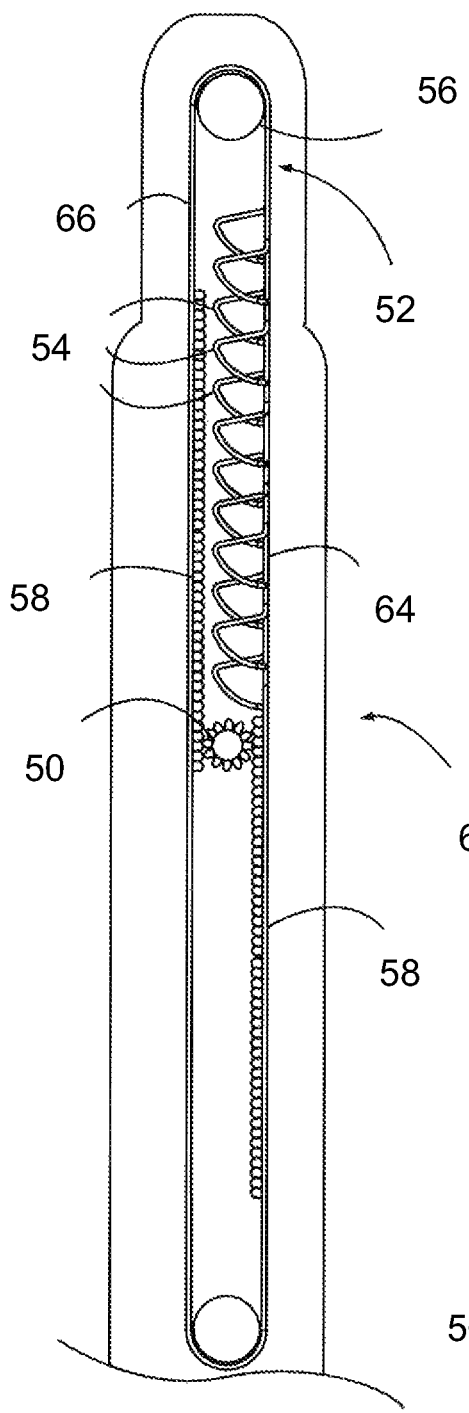
FIG. 5 illustrates a schematic view of an endocutter utilizing a feeder belt connected at each end to a different rigid rack.

Referring to FIG. 5, the Endocutter Application, among other items, discloses a feeder belt 52 to which a plurality of staples 54 are frangibly attached. The feeder belt 52 bends around a pulley 56 at its distal end. Each end of the feeder belt 52 is connected to a different rigid, toothed rack 58, and each rack engages a gear 50. The racks 58 are substantially rigid, and as a result, advancement of one rack 58 causes the gear 50 to rotate and thereby move the other rack 58 in the opposite direction. The gear 50 is located in a shaft 62 of the tool, between the handle and a distal end of the shaft. Because the racks 58 are substantially rigid, the linear travel of the racks 58 is limited by the length of the shaft 62 and of the handle connected to the shaft. Consequently, the number of firings that can be made by the tool is limited by the linear distance that the racks 58 can travel within the shaft 12 and structure connected to the shaft 12.

Continuous Feeder Belt Assembly with Flexible Rack

Figure 6:
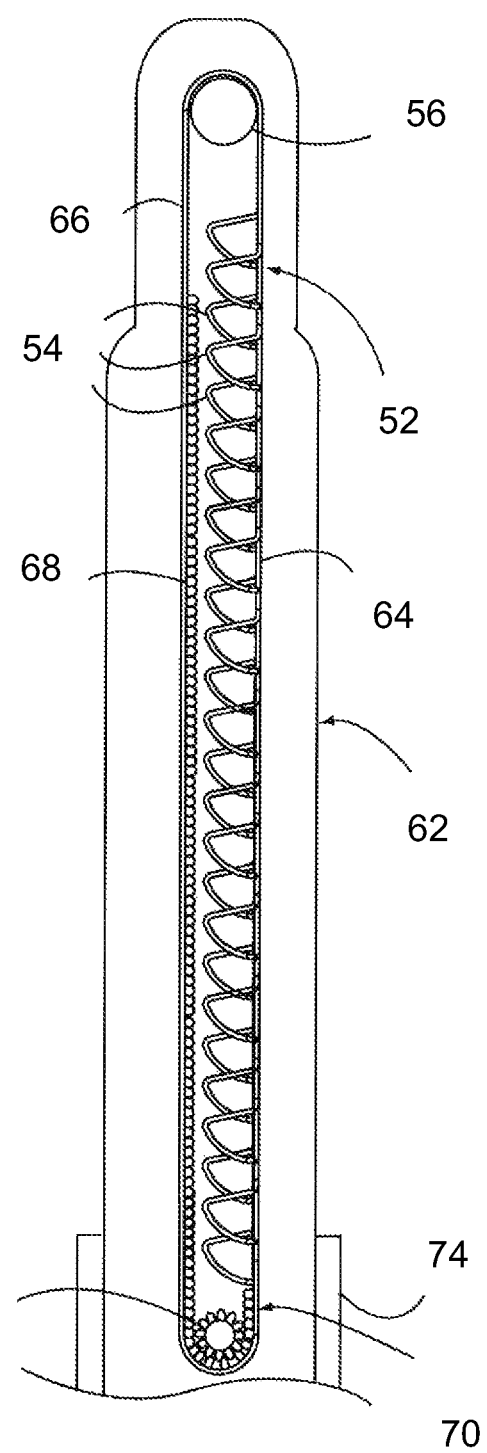
FIG. 6 illustrates a schematic view of an endocutter utilizing a feeder belt connected at each end to a single flexible rack.

Referring to FIG. 6, a feeder belt 52 bends around a pulley 56 at its distal end, such that an upper portion 64 of the feeder belt 52 is above and spaced apart from a lower portion 66 of the feeder belt 52. The upper portion 64 and lower portion 66 of the feeder belt 52 may be, but need not be, substantially parallel to one another. The upper portion 64 and lower portion 66 of the feeder belt 52 each have a proximal end, and the proximal end of each portion 64, 66 may be connected to a flexible rack 68. That is, the feeder belt 52 is connected at each end to a flexible rack 68. The combination of the feeder belt 52 and the flexible rack 68 may be referred to as the belt assembly 70. The belt assembly 70 is continuous, meaning that the belt assembly 70 defines a continuous, unbroken loop. The flexible rack 68 may be flexible in any suitable manner. As one example, the flexible rack 68 may be made from a flexible material with sufficient strength and other material properties to allow it to bend around the gear 50, and to be attached to and exert tension on the feeder belt 52. As another example, the flexible rack 68 may be a chain or other mechanism with individual, small links that are themselves rigid but that are collectively flexible. As another example, the flexible rack 68 may be fabricated from nickel-titanium alloy or other superelastic material.

Where the flexible rack 68 is utilized, the gear 50 may be located at the proximal end of the continuous belt assembly 70. In this way, the gear 50 may be utilized to tension the feeder belt 52 between the gear 50 and the pulley 56 at the distal end of the feeder belt 52. If so, the gear 50 may be located at or near the proximal end of the shaft 62, which may be held within a handle 74, or may be located proximal to or outside the shaft 62 inside the handle 74 or other structure attached to the shaft 62. Further, the initial position of the feeder belt 52 may be as shown in FIG. 6, where staples 54 extend from the upper portion 64 of the feeder belt 52 along substantially all of the upper portion 64. In this way, the feeder belt 52 is able to include more staples 54 along its length than the feeder belt 52 of FIG. 5, such that more staple firings can be made with a single feeder belt 52.

The feeder belt 52 may be assembled into an endocutter or other surgical apparatus, and may be actuated by that endocutter or other surgical apparatus, substantially as described in the Endocutter Application. Optionally, the gear 50 may be directly driven by a handle such as described in the Endocutter Application, thereby reducing the number of parts and simplifying the overall assembly relative to that handle.

Figure 7:
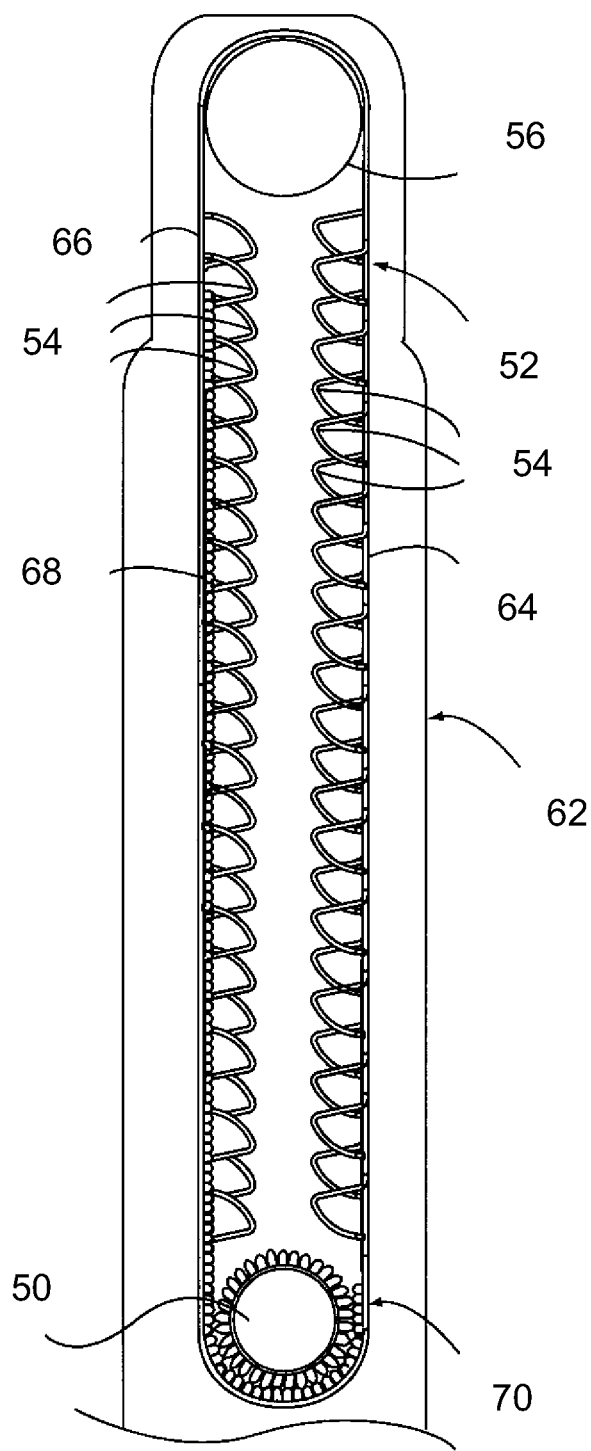
FIG. 7 illustrates a schematic view of an endocutter utilizing a feeder belt connected at each end to a single flexible rack, where staples extend from the flexible rack.

Optionally, referring also to FIG. 7, staples 54 may be frangibly connected to the flexible rack 68 as well as to the feeder belt 52. The staples 54 may be connected to the flexible rack 68 in substantially the same manner as described in the Endocutter Application. Alternately, the staples 54 may be connected to the flexible rack 68 in any other suitable manner. Where staples 54 are carried by the flexible rack 68, the upper portion 64 of the feeder belt 52 may be spaced apart from the lower portion 66 of the feeder belt 52 a distance sufficient that the staples 54 extending from each portion 64, 66 do not interfere with or engage one another. Alternately, the staples 54 instead, or also, may be laterally spaced relative to one another, such that in the initial position of the feeder belt 52, the staples 54 extending from the upper portion 64 of the continuous belt assembly 70 are laterally spaced a first distance from a longitudinal centerline of that continuous belt assembly 70, and the staples 54 extending from the lower portion 66 of the continuous belt assembly 70 are laterally spaced a second distance from a longitudinal centerline of that continuous belt assembly 70, where the first distance and the second distance are sufficiently different from one another that the staples 54 extending from different portions 64, 66 pass by one another without colliding or interfering with one another during actuating of the continuous belt assembly 70. That is, the continuous belt assembly 70 is arranged in any suitable manner such that the staples 54 along the feeder belt 52 and the flexible rack 68 of the continuous belt assembly 70 do not interfere with one another.

Alternately, where staples 54 extend from the flexible rack 68, the feeder belt 52 may be omitted, such that the flexible rack 68 is continuous and holds and deploys all of the staples 4.

Rack-Less Continuous Feeder Belt Assembly

Figure 8:
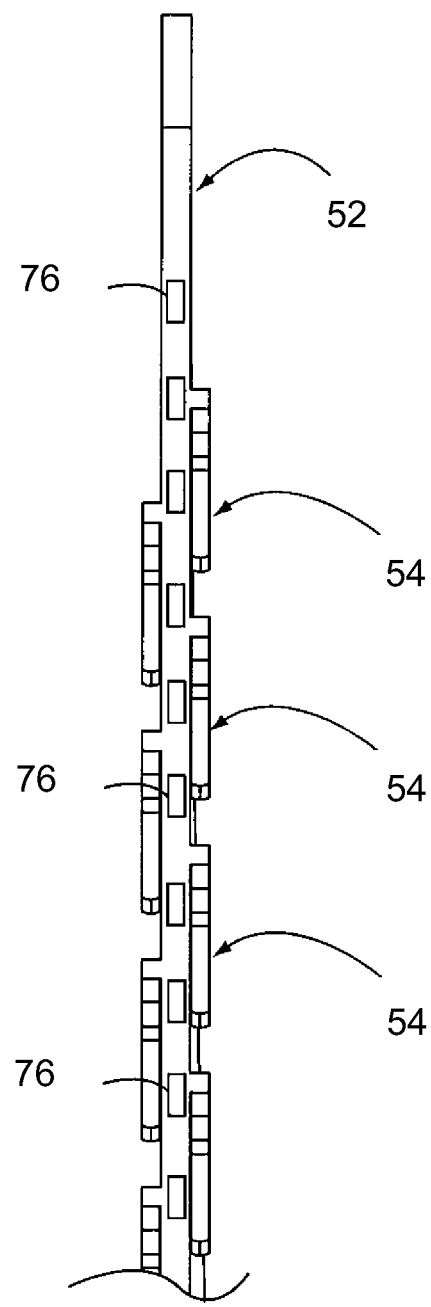
FIG. 8 illustrates a top view of an exemplary feeder belt configured to engage a gear.
Figure 9:
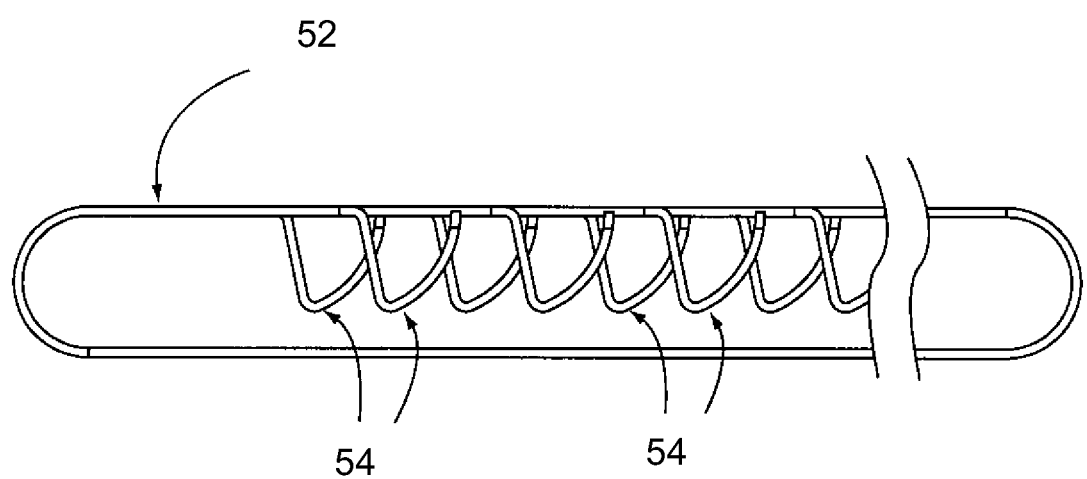
FIG. 9 illustrates a side view of an exemplary continuous feeder belt.

Referring to FIG. 8, a feeder belt 52 such as described in the Endocutter Application may include a plurality of apertures 76 defined therein. The apertures 76 may be sized, shaped and spaced apart from one another such that they engage teeth on the gear 50. The feeder belt 52 is sufficiently flexible to wrap around and be driven around the pulley 56, and consequently is sufficiently flexible to wrap around and be driven by or around the gear 50. In such an embodiment, the rack or racks 58, 68 may be omitted, and the feeder belt 52 is itself continuous and forms a continuous loop, as shown in FIG. 9. Alternately, the apertures 76 may be omitted, and the underside of the feeder belt 52 may include teeth similar to one of the racks 58, 68 configured to engage the gear 50. Alternately, the apertures 76 may be omitted, and the feeder belt 52 may be held in tension or otherwise manipulated such that the flat feeder belt 52 is capable of being advanced without the use of features on the feeder belt 52 configured to engage a gear, or without the use of a rack 58, 68 connected to or otherwise engaging the feeder belt 52.

Belt-Less Staple Chain

Figure 10:
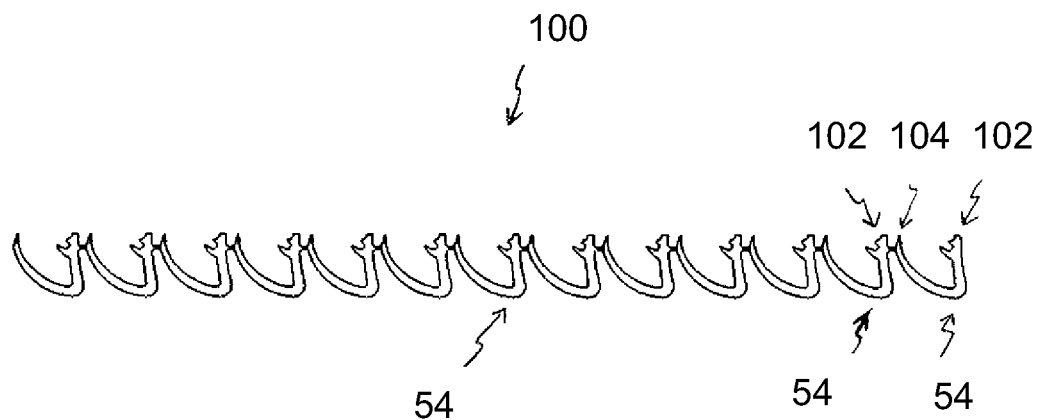
FIG. 10 illustrates a side view of an exemplary belt-less staple chain.
Figure 11:
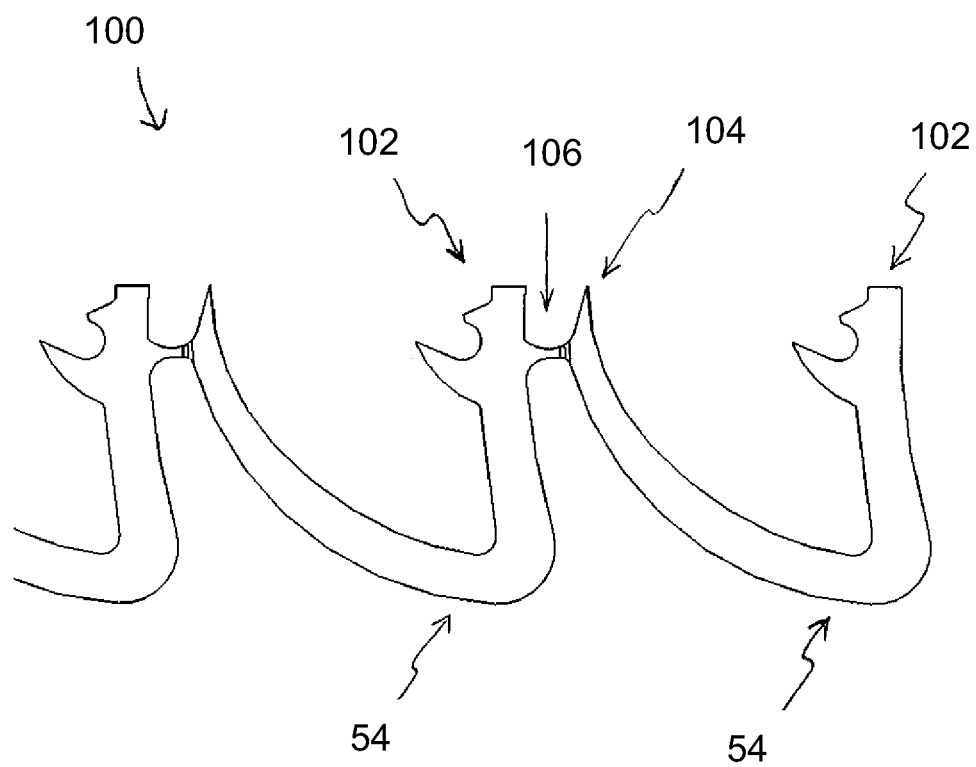
FIG. 11 illustrates a close-up side view of the exemplary belt-less staple chain.
Figure 12:
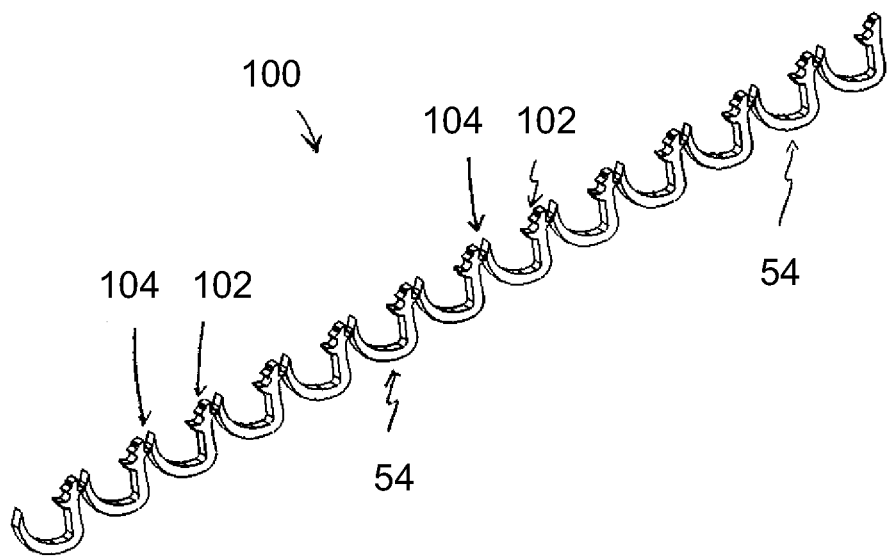
FIG. 12 illustrates a perspective view of an exemplary belt-less staple chain.
Figure 13:
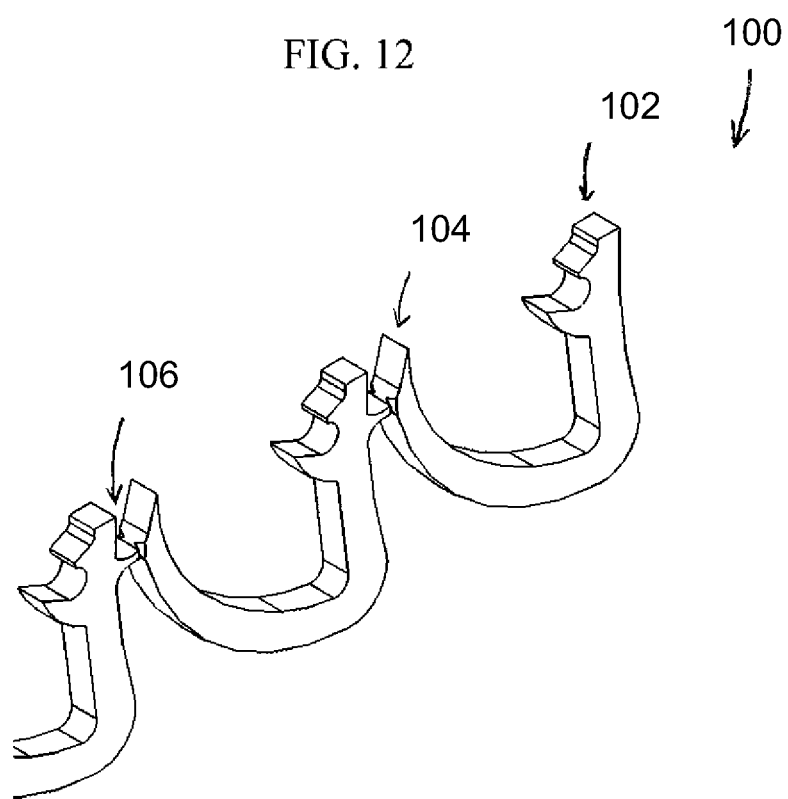
FIG. 13 illustrates a close-up perspective view of the exemplary belt-less staple chain.
Figure 23:
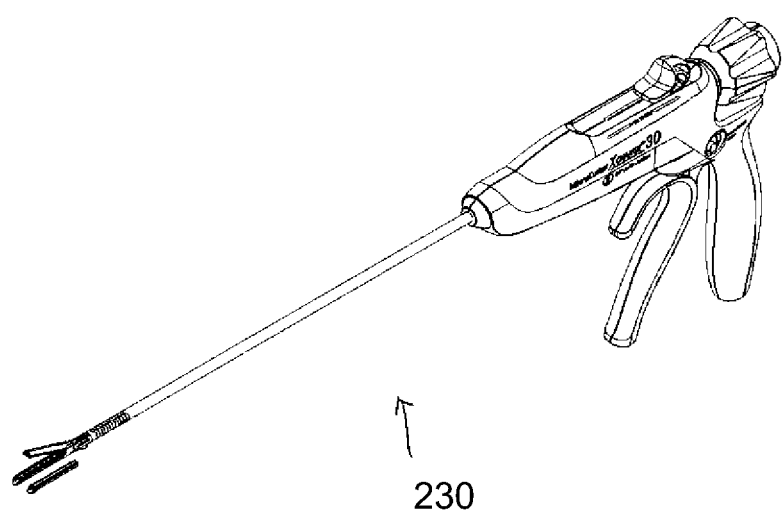
FIG. 23 illustrates one example of a stapling device using a belt-less staple chain.

Referring to FIG. 10 and FIG. 12, a continuous belt-less staple chain 100 may be used for both cartridge and cartridgeless applications in stapling devices, an example of a stapling device 230 is illustrated in FIG. 23. The belt-less staple chain 100 may not require a feeder belt, hence it is belt-less. Instead, the staples 54 are frangibly connected to each other such that they do not need to be connected to a feeder belt. For example, a substantially sharp-end or tail-end 102 of one staple 54 is frangibly connected to a substantially dull-end or head-end of the next staple 54 in the staple chain 100 at a frangible connection 106, as illustrated in FIG. 11 and FIG. 13.

Figure 14:
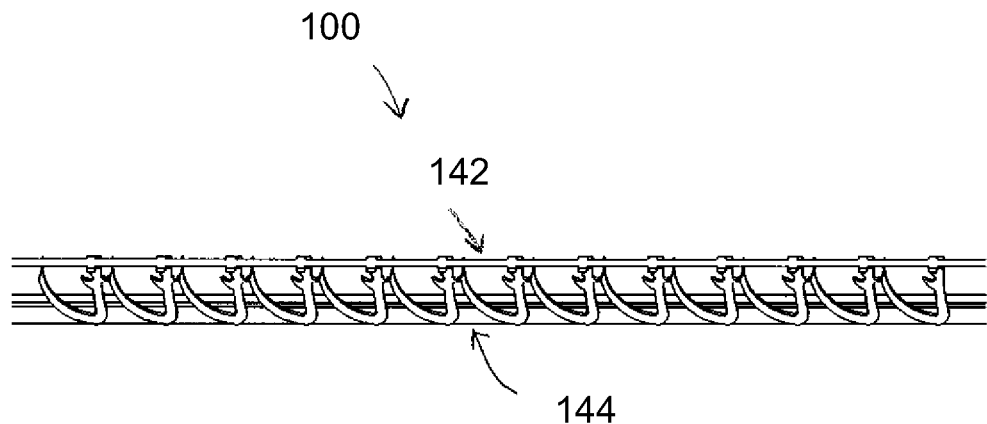
FIG. 14 illustrates one example of mounting an exemplary belt-less staple chain on a staple cartridge or mounting provisions in a cartridge-less stapling device.
Figure 15:
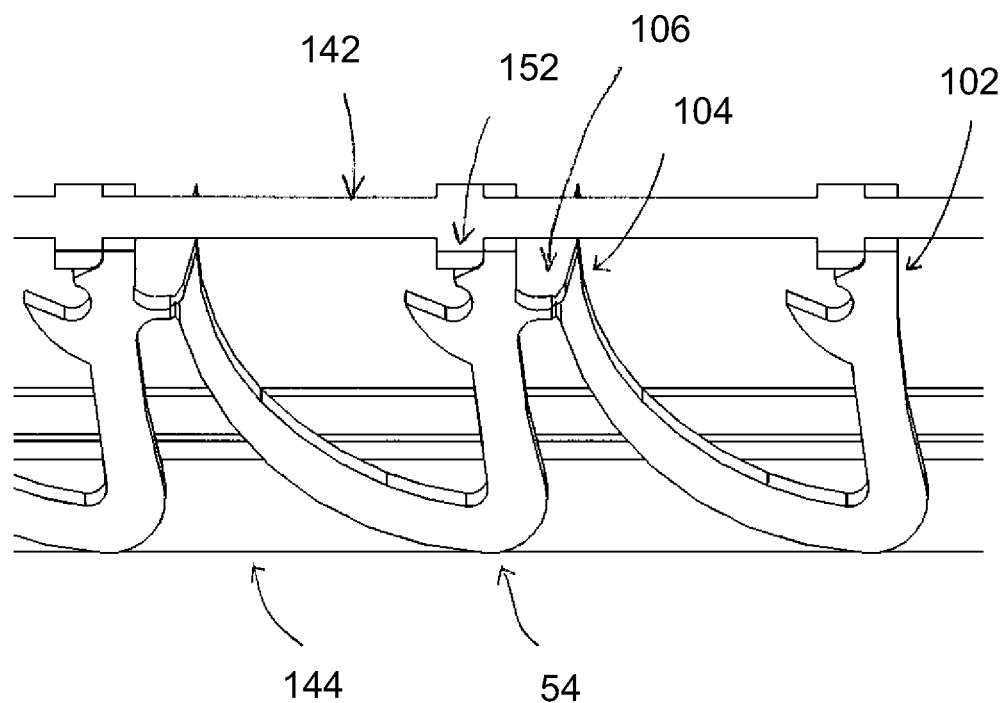
FIG. 15 illustrates a close-up view of one example of mounting the exemplary belt-less staple chain.
Figure 16:
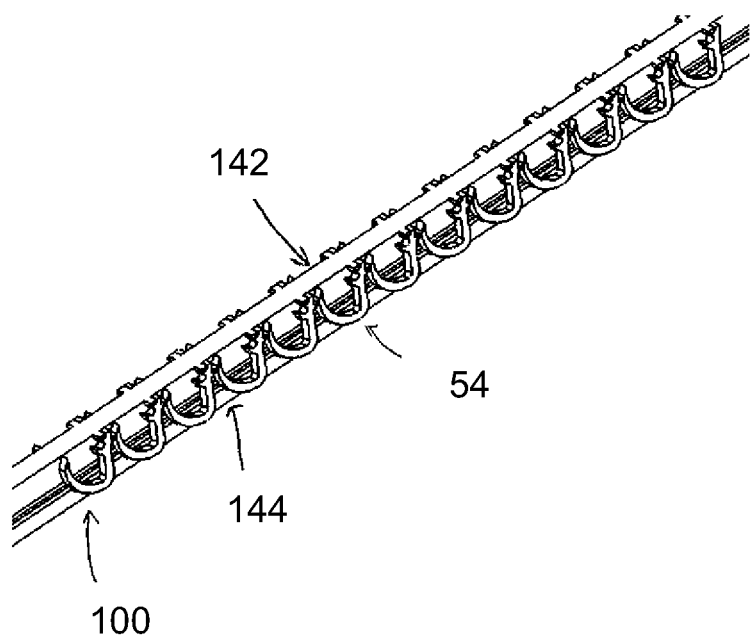
FIG. 16 illustrates a perspective view of mounting an exemplary belt-less staple chain on a staple cartridge or mounting provisions in a cartridge-less staple device.
Figure 17:
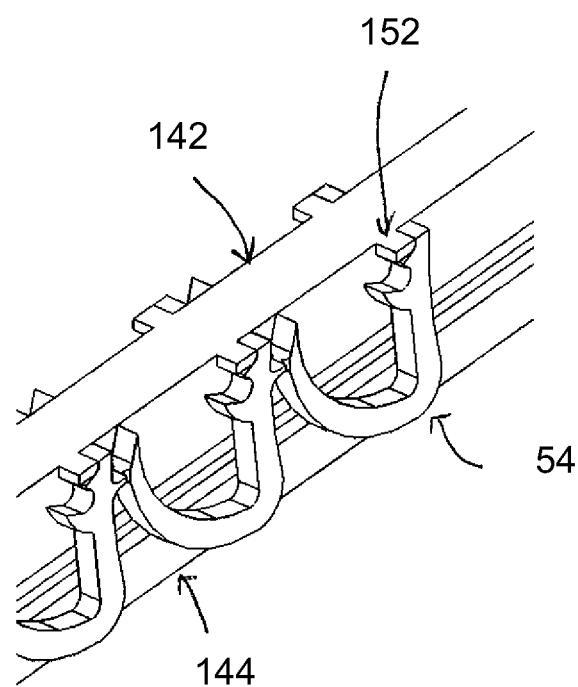
FIG. 17 illustrates a close-up perspective view of mounting the exemplary belt-less staple chain on a staple cartridge or mounting provisions in a cartridge-less staple device.

FIG. 14 and FIG. 16 illustrate one example of positioning or mounting the belt-less staple chain 100, in a cartridge or a cartridge-less system. For example, the belt-less staple chain 100 may be supported by a lateral support element 142 and a bottom support element 144, as illustrated in FIG. 14, FIG. 15, FIG. 16, and FIG. 17. The lateral support element 142 may be a support rail, a support strip, or any suitable support element that can provide lateral support to the belt-less staple chain 100. The lateral support element 142 may be an element or component of a staple cartridge, in a cartridge-based staple device. Alternatively, the lateral support element 142 may be an element or component within an application shaft of a cartridge-less based staple device. As described and can be appreciated, the bottom support element 144 may be a surface of a staple cartridge, such as a bottom surface or any surface that can provide vertical support to the belt-less staple chain 10, in either a cartridge-based staple device or a cartridge-less based staple device.

Figure 18:
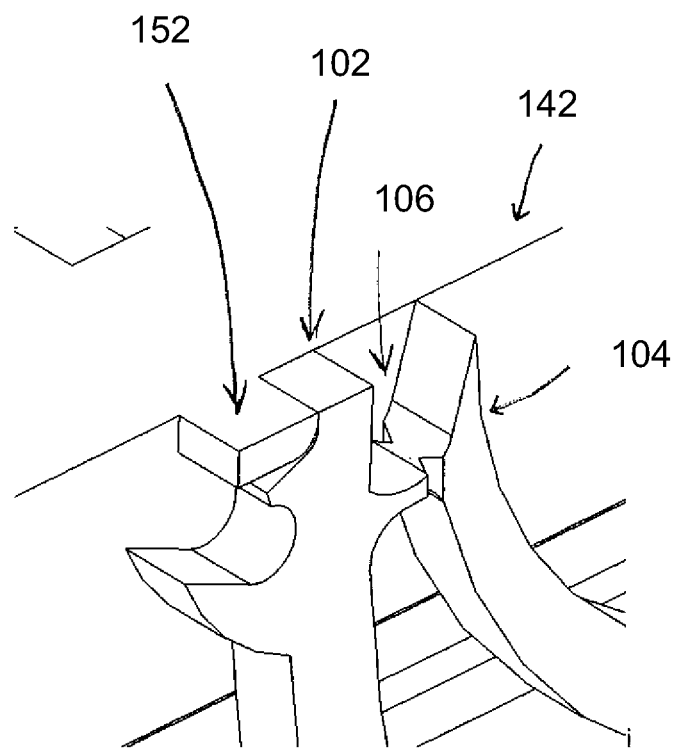
FIG. 18 illustrates a further close-up view of the belt-less staple chain and mounting provisions.

FIG. 18 illustrates a close-up view of the connection point between two staples in a belt-less staple chain 100. As illustrated, a tail-end portion 102 of a first staple 54 is connected to a head-end portion of a second staple 54 by way of a frangible connection 106. To be discussed in more detail, a stand-off element or boss element 152 (illustrated in FIG. 15 and FIG. 18) also acts as a support element to the belt-less staple chain that substantially holds the second staple 54 in place while the first staple 54 is deployed by a wedge element 194.

Figure 19A:
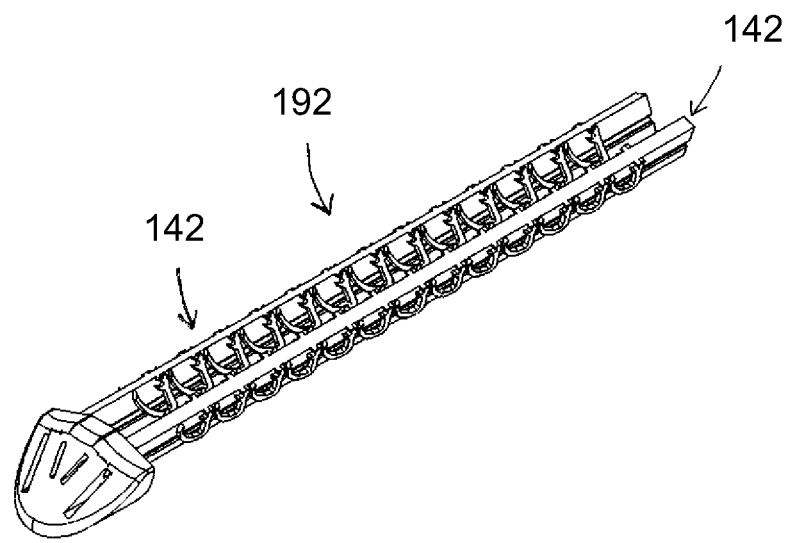
FIG. 19A and FIG. 19B illustrate one example of belt-less staple chains mounted in a staple cartridge.
Figure 19B:
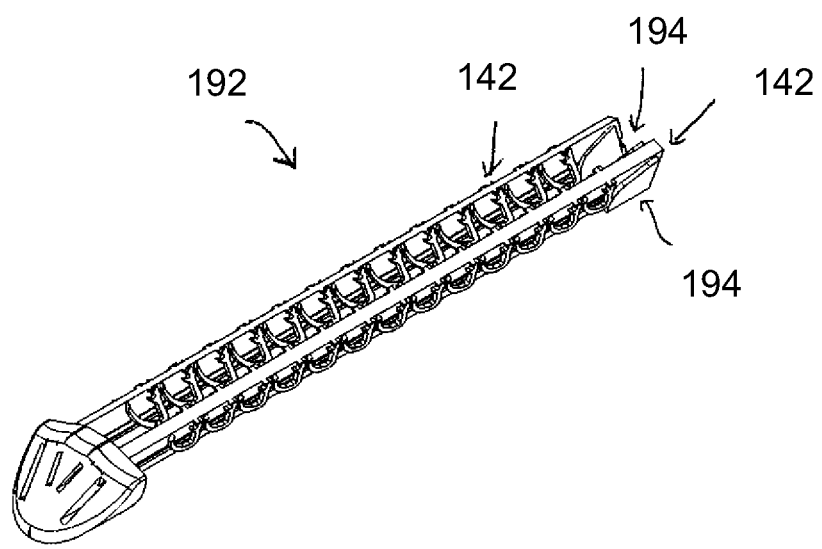

FIG. 19A and FIG. 19B illustrate one example of structural elements that may be involved in a cartridge-based staple device using the belt-less staple chain. Also, similar or equivalent structural elements may be incorporated in a cartridge-less based staple device using the belt-less staple chain. Such similar or equivalent structural elements may be incorporated into an end-effector or staple deployment component of an endocutter, as illustrated in FIG. 21 through FIG. 23.

Figure 20A:
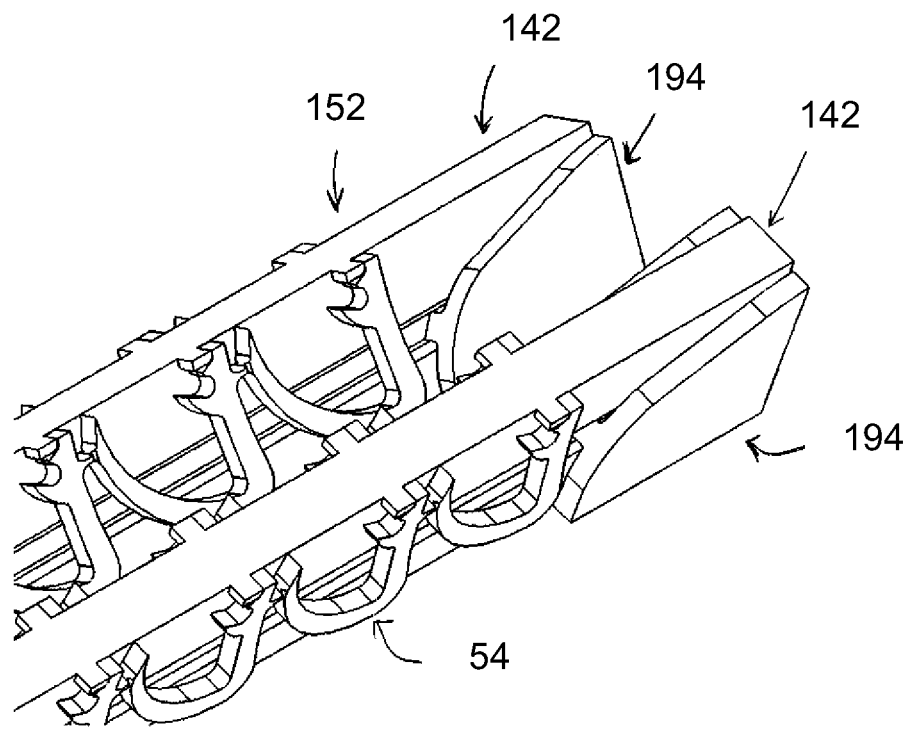
FIG. 20A through FIG. 20E illustrate staple deployment of staples on an exemplary belt-less staple chain by a wedge element.
Figure 20B:
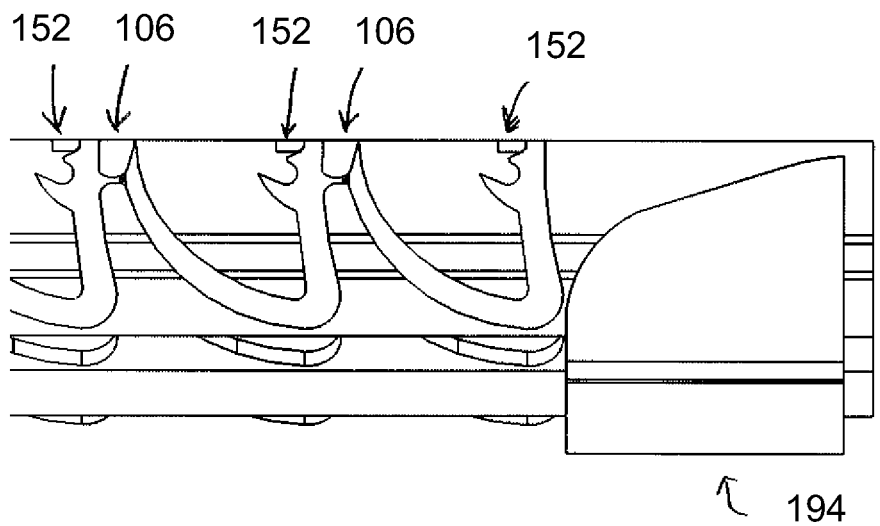
Figure 20C:
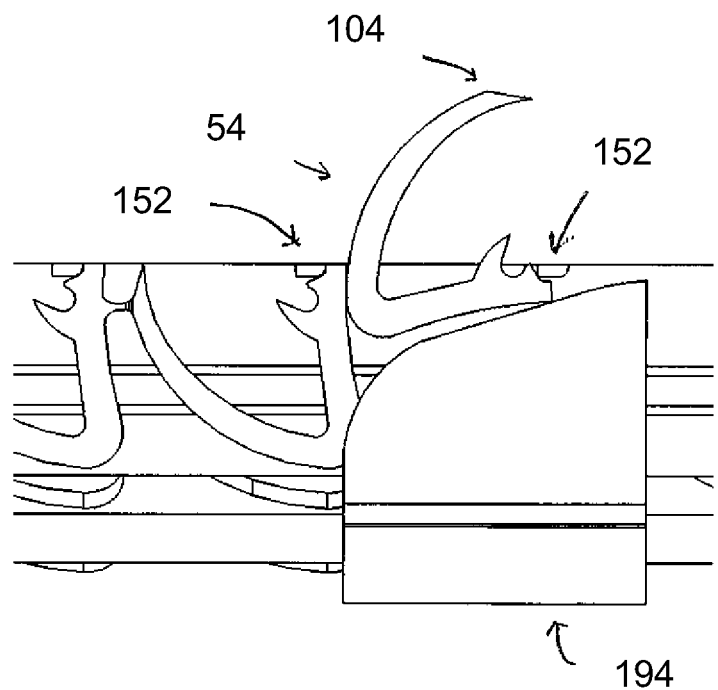
Figure 20D:
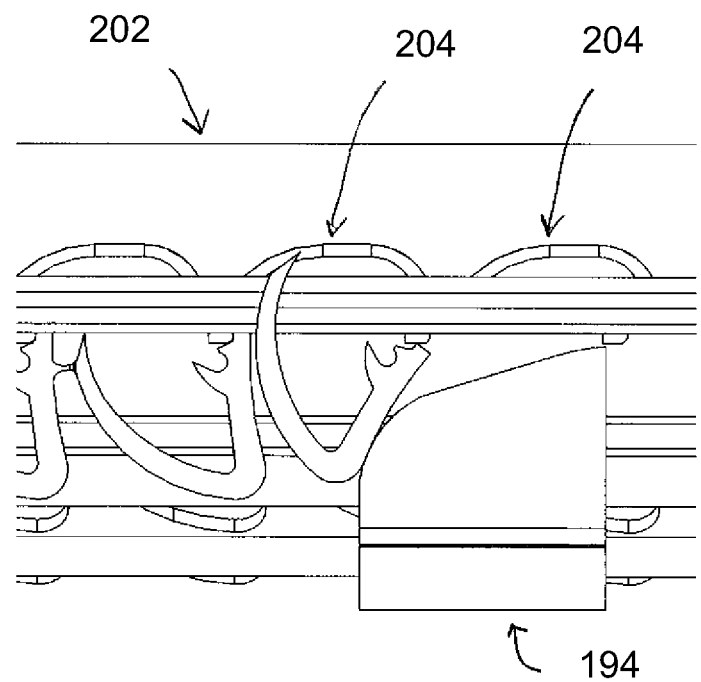
Figure 20E:
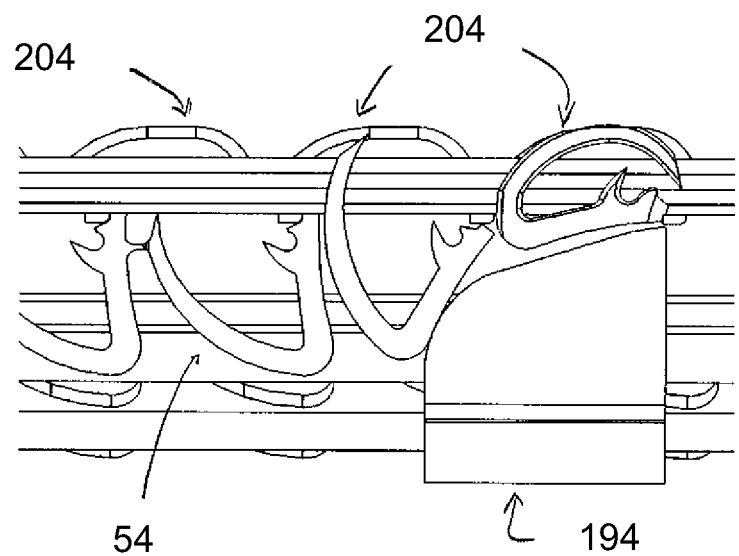

FIG. 20A through FIG. 20E illustrate one example of staple deployment process. As illustrated in FIG. 20A and FIG. 20B, the process starts with advancement of one or more wedges 194 to engage one or more staples 54 in one or more belt-less staple chains 100 in a cartridge-based or cartridge-less based staple device or system. As illustrated in FIG. 20C through FIG. 20E, the wedge element 194 may be advanced progressively forward against a first staple 54. The forward advancement of the wedge element 194 causes the head-end portion 102 of the staple 54 to pivot against the stand-off element 152 and the tail-end portion 104 to swing upwardly in a substantially arc-like motion. Referring to the close-up view of FIG. 18, the head-end portion of the second staple 54 is being held substantially in place by a corresponding stand-off element or pivot element 152, such as the upward motion of the tail-end portion of the first staple 54 is being resisted by the substantially stable or held-in-placed of the head-end portion of the second staple 54. Accordingly, as the wedge element 152 continue to urge against the first staple 54, the first staple 54 frangibly separates from the second staple 54 at the frangible connection 106 between the two staples 54, as illustrated in FIG. 20C, and the tail-end portion 104 continues its upward arc-like motion or travel. As a staple device is deployed in a surgical procedure, the upward arc-like travel of the tail-end portion 104 of the staple 54 would encounter and pierce tissue. In an application setting, as the staple 54 is deployed by the wedge element 194, the tail-end portion 104 would encounter the staple pocket elements 204 of an anvil 202 after piercing tissue. The staple pocket element 204 of the anvil 202 would deform the initially open configuration of the staple 54 into a closed staple, see FIG. 20D and FIG. 20E, thus stapling the tissue and leaving it hemostatic.

Figure 21A:
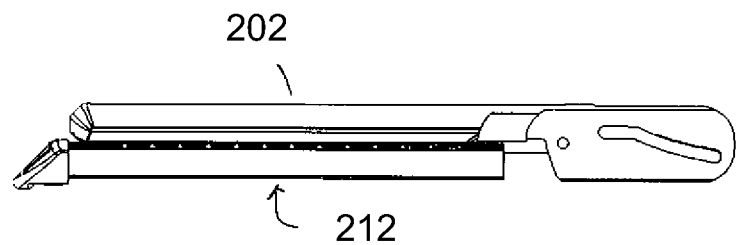
FIG. 21A and FIG. 21B illustrate one example of an end effector or distal portion of a stapling device using a belt-less staple chain.
Figure 21B:
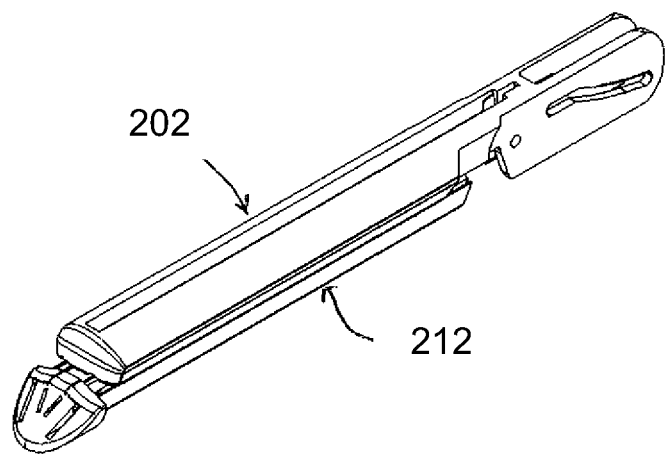
Figure 22A:
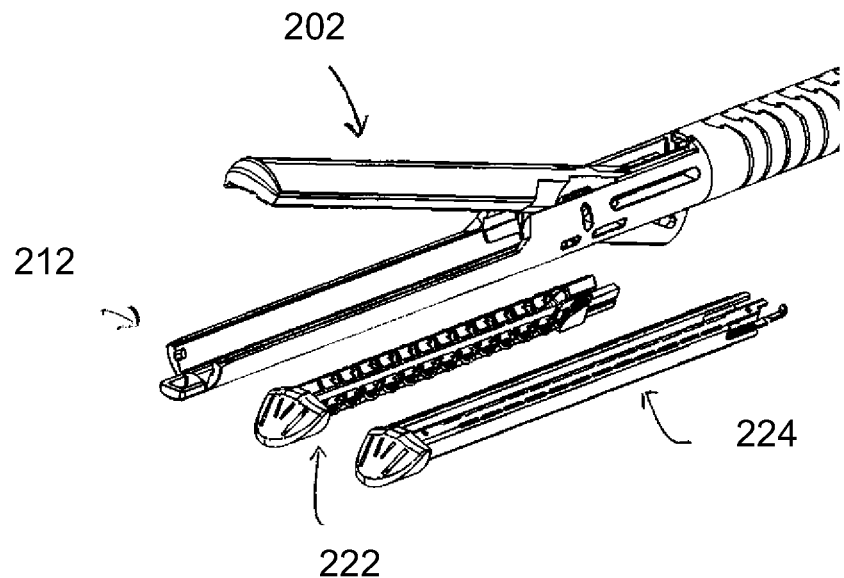
FIG. 22A and FIG. 22B illustrate another example of an end effector or distal portion of a stapling device using a belt-less staple chain.
Figure 22B:
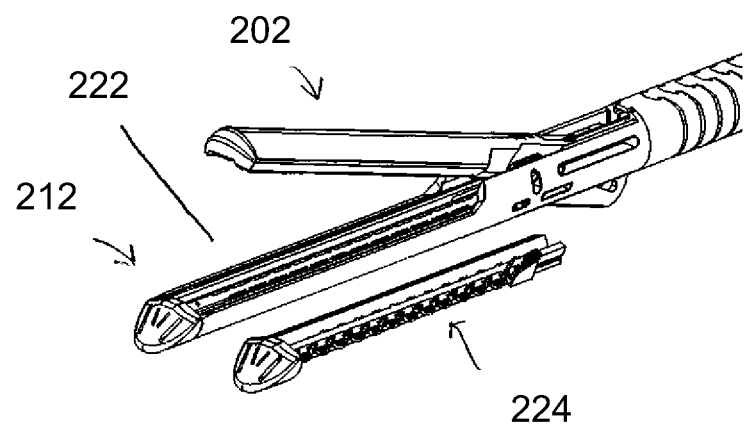

FIG. 21A and FIG. 21B illustrate an anvil element 202 and a staple holder element 212 of a staple device. Typically, a staple holder element 212 holds and deploys staples, such as one or more belt-less staple chains, and an anvil element 202 engages with one or more deployed staple 54 and deforms it from an initial configuration to a deployed configuration. An initial configuration may be an "open" configuration similar to the ones illustrated FIG. 10 through FIG. 20E. A deployed configuration may be a "closed" configuration similar to the one illustrated in FIG. 20E, where a deployed staple 54 has been deformed by a staple pocket element 204. FIG. 22A and FIG. 22B illustrate the open-jaw configuration for the anvil 202 and stapler holder 212. In the open-jaw configuration, a staple cartridge holder 224 is illustrated with its covers, shell, or skin, and separate cartridge holder 222 is illustrated without its covers, shell, or skin. FIG. 23 illustrates a staple device 230 where the belt-less staple chain 100 can be used. Similar or equivalent structural configuration and deployment arrangements are applicable to both a cartridge-base stapling device and a cartridge-less stapling device.

While the invention has been described in detail, it will be apparent to one skilled in the art that various changes and modifications can be made and equivalents employed without departing from the spirit and scope of the present invention. It is to be understood that the invention is not limited to the details of construction, the arrangements of components, and/or the methods set forth in the above description or illustrated in the drawings. Statements in this disclosure are merely exemplary; they are not and cannot be interpreted as limiting the spirit and scope of the claims. Further, the figures are merely exemplary and not limiting. Topical headings and subheadings are for the convenience of the reader only. They should not and cannot be construed to have any substantive significance, meaning or interpretation, and should not and cannot be deemed to indicate that all of the information relating to any particular topic is to be found under or limited to any particular heading or subheading. Therefore, the invention is not to be restricted or limited; instead, it is to be interpreted in accordance with the following claims and their equivalents.

What is claimed is:
1. A surgical stapling device, comprising:
   a staple holder, comprising:
      a first support element and a second support element configured to support a staple chain,
      wherein each staple of the staple chain is configured to be frangibly separated from the staple chain when each staple is deployed; and
      wherein an end portion of one of each staple of the staple chain is frangibly coupled to a head portion of another one of each staple of the staple chain; and
      a plurality of standoff members, wherein each of the plurality of standoff members is configured to support one of each staple of the staple chain when the one of each staple is being deployed.
2. The surgical stapling device of claim 1, wherein the first support element provides lateral support to the staple chain.

3. The surgical stapling device of claim 1, wherein the second support element provides vertical support to the staple chain.

4. The surgical stapling device of claim 1, wherein each of the plurality of standoff members is respectively coupled to the first support element along various locations or positions along a length or surface of the first support element.

5. The surgical stapling device of claim 1, wherein while one staple of the staple chain is deployed, each staple of a remainder of the staple chain is held in place by a respective standoff member.

6. The surgical stapling device of claim 1, wherein each staple of the staple chain is frangibly coupled to at least one other staple of the staple chain.

7. The surgical stapling device of claim 1, wherein one of each staple of the staple chain is frangibly separable from another one of each staple of the staple chain at a frangible connection region, location, or point when the one of each staple of the staple chain is being deployed.

8. The surgical stapling device of claim 7, wherein the frangible connection region, location, or point is where an end portion of one of each staple of the staple chain meets, connects, couples, or joins to a head portion of another one of each staple of the staple chain.

9. The surgical stapling device of claim 1, further comprising:
   a wedge element, deployed within the staple holder, configured to directly act on each staple of the staple chain to deploy each staple.

\* \* \* \* \*